United States Patent [19]

Friedrich et al.

[11] Patent Number: 4,802,526
[45] Date of Patent: Feb. 7, 1989

[54] CENTRIFUGAL CASTER

[75] Inventors: Ronald Friedrich, Kamp-Lintfort, Fed. Rep. of Germany; Werner Hammecke, deceased, late of Bohmte, Fed. Rep. of Germany, by Marie Elise Gisela Hammecke, heiress

[73] Assignee: Fried. Krupp GmbH, Essen, Fed. Rep. of Germany

[21] Appl. No.: 516,347

[22] Filed: Jul. 22, 1983

Related U.S. Application Data

[63] Continuation of Ser. No. 247,292, filed as PCT DE80/00114 on Aug. 2, 1980, published as WO81/00366 on Feb. 19, 1981, Pat. No. 4,418,760.

[30] Foreign Application Priority Data

Aug. 11, 1979 [DE] Fed. Rep. of Germany ....... 2932681

[51] Int. Cl.$^4$ .............................................. B22D 13/00
[52] U.S. Cl. ..................................... 164/287; 164/289
[58] Field of Search .............................. 164/287–296; 264/310, 311; 425/425; 74/574; 210/144, 360.1, 360.2; 233/23 A, 26

[56] References Cited

U.S. PATENT DOCUMENTS

| | | | |
|---|---|---|---|
| 1,805,168 | 5/1931 | Frist, Jr. ............... | 164/150 |
| 1,976,654 | 10/1934 | Carpenter ............. | 164/287 |
| 3,648,762 | 3/1972 | Hill ....................... | 164/289 |

FOREIGN PATENT DOCUMENTS

| | | |
|---|---|---|
| 204577 | 8/1907 | Fed. Rep. of Germany . |
| 593804 | 2/1934 | Fed. Rep. of Germany . |
| 1280499 | 10/1968 | Fed. Rep. of Germany . |
| 2020910 | 9/1971 | Fed. Rep. of Germany . |
| 2115042 | 9/1972 | Fed. Rep. of Germany . |
| 2019988 | 3/1976 | Fed. Rep. of Germany . |
| 2511349 | 2/1978 | Fed. Rep. of Germany . |
| 835863 | 1/1939 | France . |
| 1037630 | 9/1953 | France . |
| 10963 | of 1912 | United Kingdom . |
| 361322 | 11/1931 | United Kingdom . |

*Primary Examiner*—Kuang Y. Lin
*Attorney, Agent, or Firm*—Spencer & Frank

[57] ABSTRACT

A centrifugal caster arrangement including: a motor driven centrifuge arm and a weight arm connected to the centrifuge arm, with both arms being rotatable about a vertical axis. A counterweight is permanently fixed to the weight arm and a casting chamber is connected to the centrifuge arm. A melting crucible is disposed in the casting chamber. A plurality of muffle sets is provided with each muffle set including an exchangeable muffle cage and an associated casting muffle inserted therein. The casting chamber is provided with a region for mounting one of the muffle sets. Each exchangeable muffle cage is matched to its associated casting muffle according to size and weight so that the total weight of each respective muffle set is such magnitude that when each respective muffle set is mounted in the casting chamber and rotated about the vertical axis the centrifuge arm is in balance with the weight arm and the permanently fixed counterweight.

9 Claims, 3 Drawing Sheets

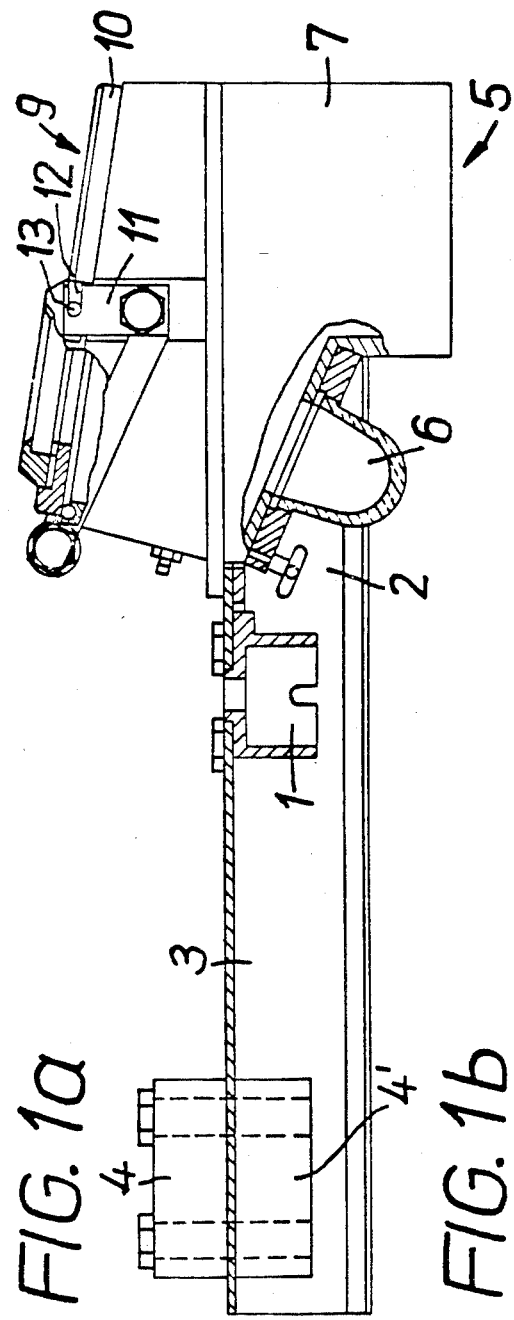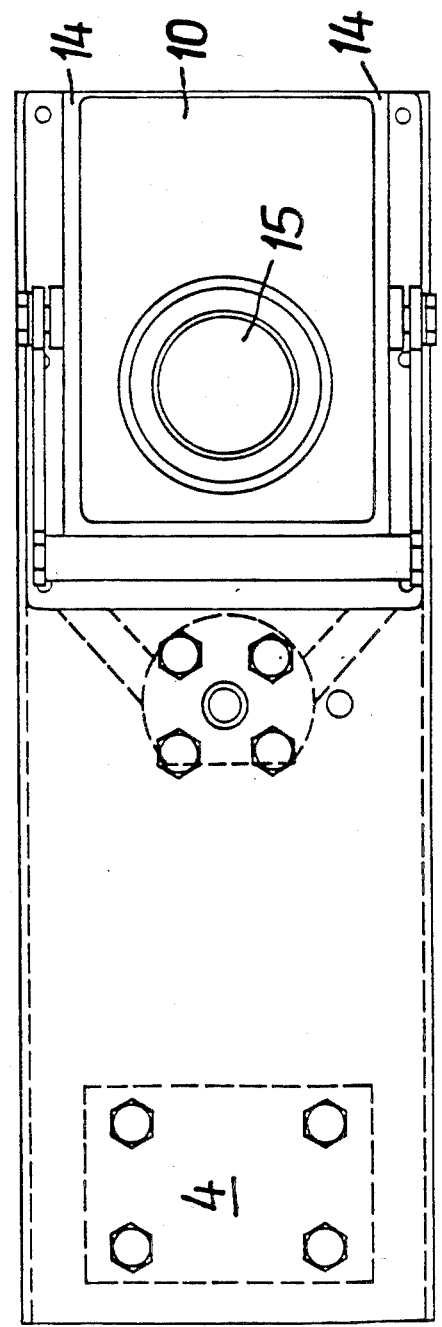

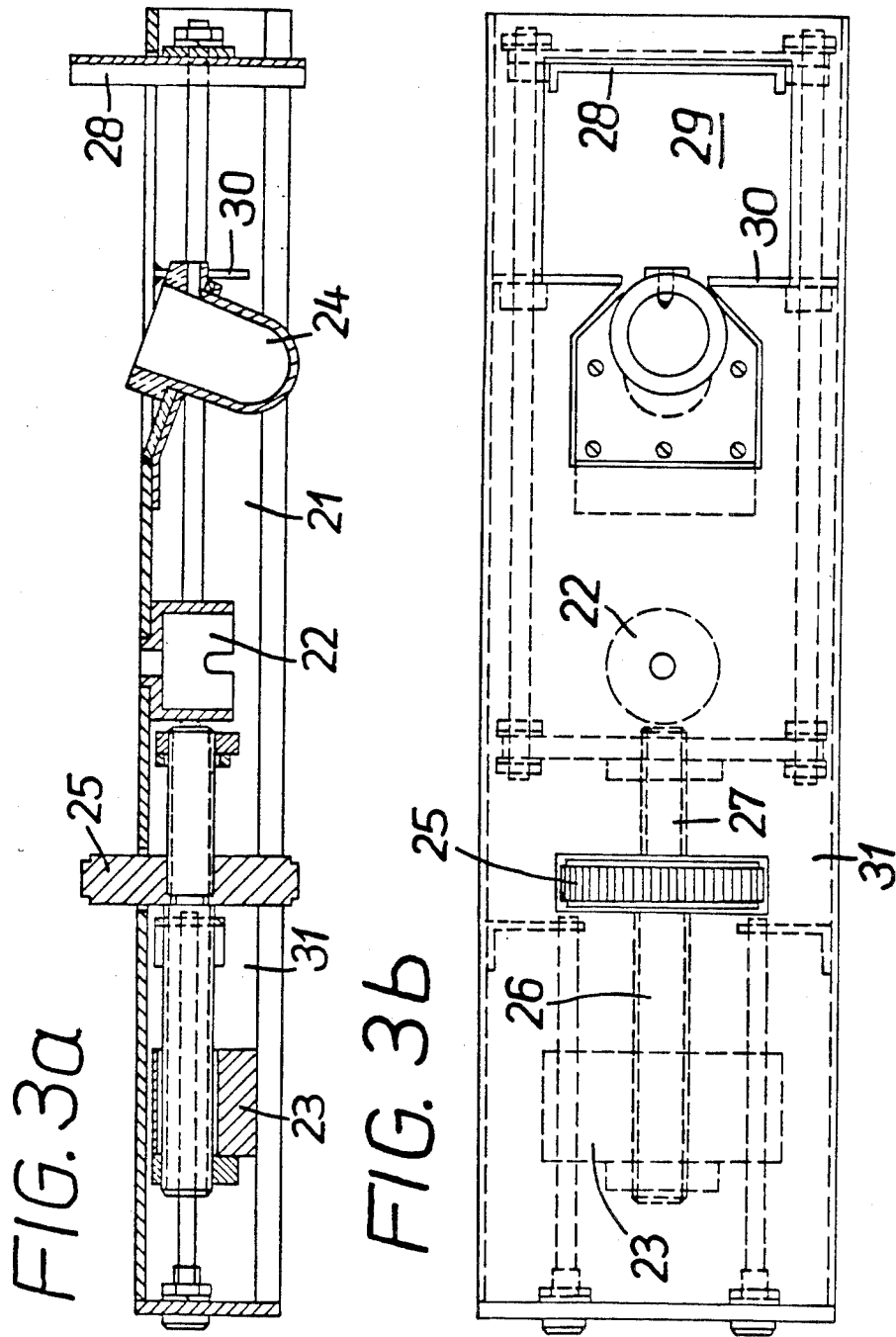

CENTRIFUGAL CASTER

This is a continuation of application Ser. No. 247,292 filed as PCT DE80/00114 on Aug. 2, 1980, published as WO81/00366 on Feb. 19, 1981, now U.S. Pat. No. 4,418,740.

BACKGROUND OF THE INVENTION

The invention relates to a centrifugal caster, particularly for dental purposes, comprising a motor driven centrifuge arm which is rotatable about a vertical axis and includes a casting chamber which, if required, may be evacuatable and in which there is disposed a melting crucible and a casting muffle mounted in a muffle cage, the caster further comprising a balance arm likewise rotatable about the same vertical axis and provided with a counterweight. Centrifugal casters of the above-mentioned type operate at rotary frequencies from 350 to 500 RPM. Therefore, after clamping in the muffle, any imbalances existing must be eliminated before the machine is put into operation. The elimination of the imbalance, on the one hand, is in the interest of the smoothest possible operation without vibratory movements which may damage the machine; on the other hand, this avoids any adverse influence on the quality of the centrifugal casting to be produced. According to the prior art, differences in weight are eliminated in that the counterweight is moved manually until a possibly existing imbalance has been compensated.

The quality of the centrifugal casting additionally depends on the temperature constancy and possibly on the quality of the vacuum in the vacuum casting chamber which must be insulated and sealed in a suitable manner.

SUMMARY OF THE INVENTION

It is an object of the present invention to provide a centrifugal caster with which the above-mentioned prerequisites for producing high quality cast alloys can be met. It is an additional object of the invention to permit easy and fast operation of the centrifugal caster even if different size casting muffles are used.

This is accomplished by a centrifugal caster wherein the counterweight is firmly attached and wherein each muffle is held in an exchangeable muffle cage that is associated with the muffle according to its size and weight. The advantage of this centrifugal caster is that the previously required tedious and time consuming setting and adjusting work at the counterweight is no longer necessary and instead the balancing can be effected more accurately. The total weight of the muffle cage with the muffle inserted is such that upon rotation of the centrifuge arm, the latter is in equilibrium with the counterweight arm. The work required before the centrifugal caster is put into operation is limited advantageously to insertion of a casting muffle into the muffle cage which is then placed into the casting chamber. Each type of casting muffle has its associated specific type of muffle cage of a certain size.

In a modification of the invention, the casting chamber is provided with cavities which are adapted to accommodate the muffle cages. For centering the muffle in the muffle cage and to further facilitate operation, supports are provided in the muffle cage. The association of the casting muffle with a particular type of muffle cage then becomes unequivocal.

The required temperature constancy is assured by double-walled muffle cages and/or muffle cages provided with a heat insulating coating or material.

To facilitate removal of the hot muffle cages from the centrifugal caster, projections are provided at the outside of the muffle cage at which a suitable tool can engage to easily lift the muffle cage together with the casting muffle. In the simplest case, such tools could be holding levers with insulated handles and a tongue which can be pushed into the projection.

According to a further feature of the invention, operation is additionally facilitated if the casting chamber—particularly if it is a vacuum chamber—is provided with a cover which can be arrested by means of a lever lock. Advantageously the cover is provided with seals at its contact faces and is provided with a viewing pane.

However, the problem on which the invention is based is solved equally as well by a centrifugal caster in which the counterweight and the inserted casting muffle are each disposed in a guide carriage which can be moved horizontally over the axis of the centrifuge arm or the axis of the weight arm, respectively, both carriages being movable by a single setting device. This centrifugal caster also has the advantage that it can be operated without lengthy adjustment of the counterweight. Operating errors are avoided in a simple manner.

According to a further feature of the invention, the centrifugal caster is provided with a hand wheel as the setting device with which the guide carriages can be displaced via two spindles having different, oppositely oriented threads. After insertion, the muffle is clamped in by rotating the hand wheel which simultaneously aligns the counterweight by means of the second spindle. If different size muffles, which thus also have different weights, also differ in length, i.e., the heavier muffles are also correspondingly longer, the centrifugal caster according to the invention permits the use of any desired muffle size, a decision having to be made as to a certain shape of the muffle. Opening or closing, respectively, of the muffle mount on the guide carriage automatically aligns the counterweight.

BRIEF DESCRIPTION OF THE DRAWING

FIG. 1a is a cross-sectional view of the centrifuge arm of a centrifugal caster in accordance with the invention;

FIG. 1b is a top view of the centrifuge arm of FIG. 1a;

FIGS. 3a is a cross-sectional view of a different embodiment of a centrifuge arm of a centrifugal caster in accordance with the invention; and FIG. 3b, a top view of the centrifuge arm of FIG. 3a.

DETAILED DESCRIPTION OF THE PREFERRED EMBODIMENT

Figure 2A:
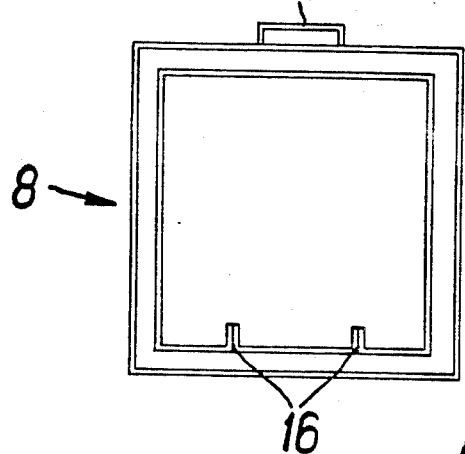
FIGS. 2a and 2b show a muffle cage in cross section and longitudinal section, respectively.

The centrifugal caster shown in FIGS. 1a and 1b essentially includes a centrifuge arm 2 mounted on a motor-driven shaft 1 and a weight arm 3 with counterweights 4 and 4'. A casting chamber 5, which includes a melting crucible 6 and a chamber 7 for accommodating a muffle cage 8 (see FIGS. 2a and 2b), is disposed on centrifuge arm 2. An upper side 9 of casting chamber 5 is further provided with an opening which can be closed by means of a cover 10. In order to open and close casting chamber 5, cover 10 is actuated via a lever 11 and can be arrested by means of slots 12 in cover 10 and pins 13 at casting chamber 5. If casting chamber 5 is designed as a vacuum casting chamber, seals 14 are additionally provided at casting chamber 5. Advisably, cover 10 is provided with a viewing pane 15 which may be tinted if required.

Figure 2B:
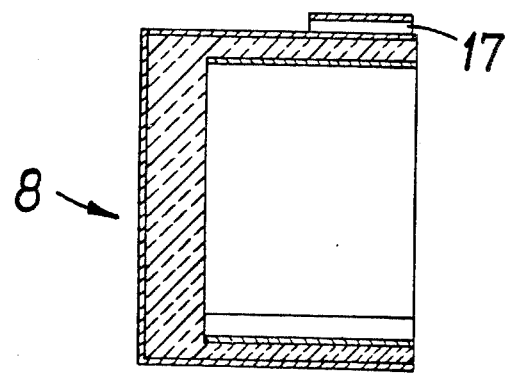
Figure 2C:
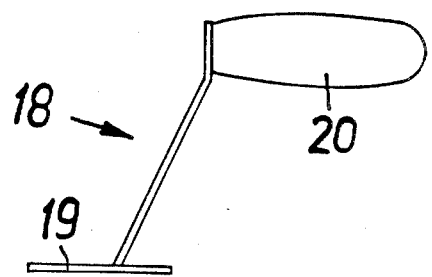
FIG. 2c is a holding lever for holding the muffle cage according to FIGS. 2a and 2b.

A muffle set comprising an exchangeable muffle cage 8 and a casting muffle 32 are shown in FIGS. 2a and 2b. Muffle cage 8 has a cube shape and is equipped with supports 16 for the casting muffles 32 so as to center the casting muffles 32 while they are being inserted, and with a projection 17. An arrangement for a casting cavity 33 within a casting muffle 32 is also shown in FIGS. 2a and 2b. A tongue 19 of holding lever 18 shown in FIG. 2c can be pushed into the projection 17 so as to facilitate transport of muffle cage 8. Holding lever 18 is provided with as handle made of wood or that is otherwise heat-insulated.

The apparatus sketched in FIGS. 1 and 2 is easy to operate. Depending on the muffle employed, the associated, matching muffle cage 8 is located which is then placed into chamber 7. Thereafter, the casting member 5 is closed by means of cover 10 and by actuation of lever 11. The production of a centrifugal casting known in the art can thus begin.

As an alternative to the centrifugal caster illustrated in FIGS. 1a and 1b, the centrifugal caster shown in FIGS. 3a and 3b can also be used. This caster essentially also comprises a centrifugearm 21 fastened on a shaft 22, a weight arm 31 with counterweight 23 as well as a melting crucible 24. The casting chamber is not shown, but is designed to correspond to FIG. 1. However, the centrifugal caster differs in the device for setting the rotational equilibrium. This is accomplished by a hand wheel 25, the rotation of which on two differently threaded spindles 26 and 27 causes the simultaneous displacement of a counterweight 23 and of holding wall 28 of guide carriage 29, respectively, into which a casting muffle can be inserted.

The centrifugal caster according to FIGS. 3a and 3b is likewise easy to operate. The casting muffle is inserted into guide carriage 29, whereupon hand wheel 28 is actuated until the muffle has been firmly clamped between the wall 30 of guide carriage 29 and holding wall 28. At the same time, counterweight 23 is moved via spindle 26 into the position corresponding to a weight equalization. The centrifugal casting then can be produced.

We claim:

1. A centrifugal caster arrangement comprising: a motor driven centrifuge arm; a casting chamber connected to said centrifuge arm; a weight arm connected to said centrifuge arm, both said arms being rotatable about a vertical axis; a counterweight having a permanently fixed position relative to said weight arm and being immovable relative to said casting chamber and said vertical axis; a melting crucible disposed in said casting chamber; and a plurality of muffle sets, each said muffle set comprising an exchangeable muffle cage and an associated casting muffle inserted in said exchangeable muffle cage, wherein said casting chamber is provided with a region for mounting one of said muffle sets, and each said exchangeable muffle cage is matched to its associated casting muffle according to size and weight so that the total weight of each respective muffle set is of such magnitude that when each respective muffle set is mounted in said casting chamber and rotated about said vertical axis said centrifuge arm is in balance with said weight arm and said permanently fixed counterweight.

2. An arrangement according to claim 1 wherein said casting chamber is evacuatable.

3. An arrangement according to claim 1 wherein each said exchangeable muffle cage includes supports for centering a respective one of said casting muffles therein.

4. An arrangement according to claim 1 wherein each said exchangeable muffle cage has double walls.

5. An arrangement according to claim 1 wherein each said exchangeable muffle cage includes heat insulating material.

6. An arrangement according to claim 1 wherein each said exchangeable muffle cage includes at least one projection on the outside thereof.

7. An arrangement according to claim 1 and further including a cover for covering said casting chamber and a lever lock for arresting said cover.

8. An arrangement according to claim 7 wherein said cover has a contact face which faces said casting chamber and said casting chamber includes a seal adjacent said contact face.

9. An arrangement according to claim 8 wherein said cover includes a viewing pane.

* * * * *